United States Patent
Altschuler et al.

[11] Patent Number: 5,840,040
[45] Date of Patent: Nov. 24, 1998

[54] ENCEPHALOLEXIANALYZER

[75] Inventors: Eric L. Altschuler, Livermore; Farid U. Dowla, Castro Valley, both of Calif.

[73] Assignee: The Regents of the University of California, Oakland, Calif.

[21] Appl. No.: 993,050

[22] Filed: Dec. 18, 1992

[51] Int. Cl.$^6$ ................................................ A61B 5/00
[52] U.S. Cl. ...................................... 600/545; 600/544
[58] Field of Search .................................. 128/731, 732; 600/545, 544

[56] References Cited

U.S. PATENT DOCUMENTS

| | | | |
|---|---|---|---|
| 3,032,029 | 5/1962 | Cunningham | 128/732 |
| 3,826,243 | 7/1974 | Anderson | 324/76.13 |
| 3,877,466 | 4/1975 | Montor | 128/732 |
| 4,013,068 | 3/1977 | Settle et al. | 128/732 |
| 4,228,806 | 10/1980 | Lidow | 128/731 |
| 4,228,807 | 10/1980 | Yagi et al. | 128/732 |
| 4,334,545 | 6/1982 | Shiga | 128/732 |
| 4,354,505 | 10/1982 | Shiga | 128/732 |
| 4,493,539 | 1/1985 | Cannon, Jr. | 351/205 |
| 4,800,893 | 1/1989 | Ross et al. | 128/732 |
| 4,832,480 | 5/1989 | Kornacker et al. | 351/246 |
| 4,846,190 | 7/1989 | John | 128/731 |
| 4,869,264 | 9/1989 | Silberstein | 128/731 |
| 5,083,571 | 1/1992 | Prichep | 128/731 |

FOREIGN PATENT DOCUMENTS

| | | | |
|---|---|---|---|
| 8901313 | 2/1989 | WIPO | 128/731 |

OTHER PUBLICATIONS

Silverman et al, "A Hybrid Broad Band EEG Frequency Analyzer . . . Experiments" Jan. 1973, vol. BME–20, No. 1, pp. 60–62.

"Researchers trying to develop computer controlled by mind" Triv–Valley Herald, Business Section, Jul. 27, 1993. Author unknown.
Handbook of EEG and Clinical Neurophysiology, A. Remond (Ed.), vol. 6, Part A, 1976, pp. 6A–35, 36, 56, 57.
W. Kuhlman, "Functional Topography of the Human Mu Rhythm, "EEG and Clinical Neurophysiology, 1978, 44:83–93.
Principles of Neural Science (Third Ed.), Kandel et al. (ed.), pp. 10, 372. Date unknown.
J. R. Wolpaw et al., "An EEG–based Brain–Computer Interface for Cursor Control", Electroencephalography and Clinical Neurophysiology, 1991, 78: 252–259.

*Primary Examiner*—Guy V. Tucker
*Attorney, Agent, or Firm*—Henry P. Sartorio

[57] ABSTRACT

The encephalolexianalyzer uses digital signal processing techniques on electroencephalograph (EEG) brain waves to determine whether or not someone is thinking about moving, e.g., tapping their fingers, or, alternatively, whether someone is actually moving, e.g., tapping their fingers, or at rest, i.e., not moving and not thinking of moving. The mu waves measured by a pair of electrodes placed over the motor cortex are signal processed to determine the power spectrum. At rest, the peak value of the power spectrum in the 8–13 Hz range is high, while when moving or thinking of moving, the peak value of the power spectrum in the 8–13 Hz range is low. This measured change in signal power spectrum is used to produce a control signal. The encephalolexianalyzer can be used to communicate either directly using Morse code, or via a cursor controlling a remote control; the encephalolexianalyzer can also be used to control other devices. The encephalolexianalyzer will be of great benefit to people with various handicaps and disabilities, and also has enormous commercial potential, as well as being an invaluable tool for studying the brain.

18 Claims, 6 Drawing Sheets

|  | CH 1 |
|---|---|
| REST | HIGH |
| MOVEMENT OR MOVEMENT REHEARSAL | LOW |

FIG. 7A

|  | CH 1 | CH 2 |
|---|---|---|
| REST | HIGH | HIGH |
| MOVEMENT OR MOVEMENT REHEARSAL RIGHT REST LEFT | LOW | HIGH |
| MOVEMENT OR MOVEMENT REHEARSAL LEFT, REST RIGHT | HIGH | LOW |
| MOVEMENT OR MOVEMENT REHEARSAL RIGHT AND LEFT | LOW | LOW |

FIG. 7B

ENCEPHALOLEXIANALYZER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The invention relates generally to detecting signals from the human brain and more particularly to interpretation and utilization of signals from the brain for communication and for control of machines.

The motor cortex of the human brain is the major area which controls body movement. Electrical stimulation of the motor areas elicits movement, and the activity of cells in these areas is closely related to body movement. Beginning at the mid-line of the brain and proceeding laterally, there is an orderly array of motor points for the legs, trunk, and arms, with two discontinuities for the hands and face. The topographical relations may be represented by a distorted body figure known as the "humunculus" or "little man". Disproportionate areas of the motor cortex are devoted to different muscles. The muscles of the fingers, lips and tongue, which are involved in delicate, precise movements, have relatively large cortical areas devoted to their control, while comparatively smaller cortical areas are devoted to other body parts, as shown by the distortion of the humunculus.

Electroencephalography (EEG) is the recording of minute electric currents produced by the brain. The technique, discovered in 1929, was found to have important clinical significance for the diagnosis of brain disease. The recording machine, or electroencephalograph (EEG), produces a record of brain waves, the electroencephalogram (EEG). About 20 electrodes are placed on the scalp in accordance with standard positions adopted by the International Federation of EEG, called the 10/20 System. Electrical voltage is transduced from the scalp by differential input amplifiers and amplified to drive the EEG. The EEG waves are defined by form and frequency. Various frequencies are given Greek letter designations. The EEG reveals functional abnormalities of the brain.

A number of different systems have been developed which measure brain signals. The following patents represent several brain wave measurement systems as well as other signal processing methods.

U.S. Pat. No. 5,092,343 to Spitzer et al. is directed to a waveform analysis apparatus and method using neural network techniques to classify diseased versus normal EEG signals.

U.S. Pat. No. 4,947,480 to Lewis is directed to multi-channel signal enhancement by signal processing.

U.S. Pat. No. 4,907,597 to Chamoun is directed to a cerebral biopotential analysis system and method. It is primarily directed to a display and plotting device.

U.S. Pat. No. 4,753,246 to Freeman to an EEG spatial filter and method, with multi-channel EEG data analysis.

U.S. Pat. No. 4,603,703 to McGill et al. is directed to a method for real time detection and identification of neural electric signals to determine the proportion of signals emanating from nerve, muscle, and brain tissue, but not to study EEG signals.

U.S. Pat. No. 4,579,125 to Strobl et al. is directed to a real time spectral analyzer.

U.S. Pat. No. 4,493,327 to Bergelson et al. is directed to an automatic evoked potential detection system for evoked responses from external sensory stimulus.

U.S. Pat. No. 4,094,307 to Young, Jr. is directed to a method and apparatus for aiding in the anatomical localization of distinctions in a brain using visual evoked responses to study disfunctional brains.

Neuroscientists are engaged in studying the relationship between nerve cells and consciousness, as illustrated by the article by Sandra Blakeslee, "Nerve Cell Rhythm May be Key to Consciousness", New York Times, Tuesday, Oct. 27, 1992.

Although considerable work has been done in the areas of measuring and diagnosing the brain, no system has been developed which allows machines to be controlled by signals from the human brain or to allow a person to easily communicate over a channel using brain waves. This would be of tremendous advantage to people with various handicaps and disabilities as well as having numerous scientific and industrial applications.

SUMMARY OF THE INVENTION

Accordingly, it is an object of the invention to provide method and apparatus for interpreting and utilizing signals from the human brain for mental communication and thought control of machines.

It is a further object of the invention to provide method and apparatus which can be controlled by simple thought.

It is also an object of the invention to provide a simple method and apparatus, which require no training and no external operator.

It is another object of the invention to provide method and apparatus to study cognitive tasks from brain wave signals which is much lower cost, easier and non-invasive compared to presently available methods.

The present invention provides a quantum leap to the twenty-first century. The invention is method and appartus for detecting, interpreting and utilizing brain wave signals for communication and for thought control of machines, e.g., a thought typewriter. In a basic embodiment, the invention is a two state system based on the movement rehearsal paradigm. The invention measures the decrease in the mu wave from the rest state (maximum value) when not moving and not thinking about moving to an active state caused by movement or thinking about movement.

The invention detects brain waves, i.e. electroencephalogram (EEG) signals, to determine whether a person is a) moving or thinking about moving, or b) not moving and not thinking about moving. A pair of electrodes are placed over the motor cortex on the central region of the scalp on opposite sides of the head. The EEG machine records the potential difference between these two electrodes. When a person is resting, i.e., not moving and not thinking about moving, there is a large wave, known as the mu wave, present typically in the 8–13 Hz region. When the person moves, or thinks about moving, a suitable body part the wave substantially decreases. Thus the system operates on the basis of mu wave attenuation caused by actual movement or movement rehearsal (thinking of moving). Digital signal processing of the EEG wave is used to produce a control signal, which can be used to communicate or actuate various machines.

In the simplest embodiment, the system is a binary or "on-off" system. Although many different body parts could be used, parts such as the hands and feet appear best. The fingers are a particularly suitable body part since movement or movement rehearsal of the fingers produces a reliable signal (a large change in the mu wave). In additional embodiments, more than two electrodes can be used, measurements can be taken on either side of the head to provide independent "left-right" control, or measurements can be taken at particular positions on the head to obtain the effect caused by different body parts. Intermediate mu wave blocking by different body parts, or a left-right scheme, may be used to provide more than a two state system. The multiple state system can be based on movement or movement rehearsal of one body part, e.g. the right hand, while consciously relaxing another body part, e.g. the left hand.

DETAILED DESCRIPTION OF THE PREFERRED EMBODIMENTS

The invention provides a simple method and apparatus based on using the movement rehearsal paradigm repeatedly to produce a sequence of communication or control signals. The movement rehearsal paradigm is the decrease or attenuation in the mu wave from rest when the mu wave is at its maximum value to a lower value when the person is moving or thinking of moving a part of the body, e.g. fingers. Each element or "bit" of the control signal is generated by being in the appropriate state (rest or movement) for a predetermined time interval.

The encephalolexianalyzer uses digital signal processing techniques on electroencephalograph (EEG) brain waves to determine whether someone is thinking about moving or not thinking about moving. The movement in an illustrative preferred embodiment is tapping the fingers. Alternatively, similar results can be obtained by actually moving or not moving and not thinking about moving. The decrease in the EEG (mu) wave caused by either movement or movement rehearsal (thinking of movement) is used to produce a control signal. A simple application is to control an on-off switch, e.g. to turn a light on or off. The encephalolexianalyzer can be used to communicate either directly, e.g. using Morse code, or via a cursor controlling a remote control. The encephalolexianalyzer can also be used to control other devices.

Figure 1:
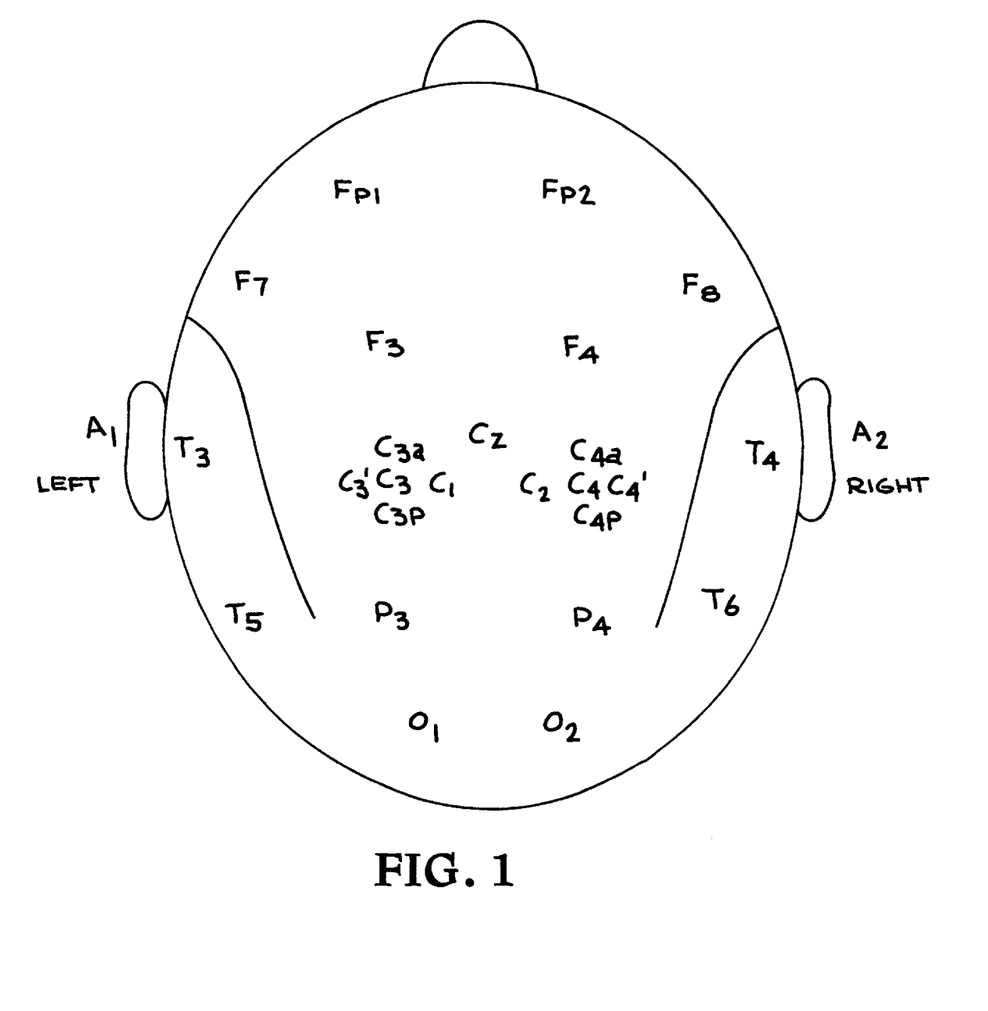
FIG. 1 is a top view of a human head showing placement of the electrodes.

The encephalolexianalyzer works as follows: A pair of electrodes are placed substantially over the motor cortex, one on each side of the head so that an EEG brain wave signal can be measured. Alternatively, a single measurement electrode can be used with a reference electrode. Preferably, the EEG is recorded from the standard $C_3$ and $C_4$ positions in the central region of the scalp as shown in FIG. 1. A strong signal, with good signal to noise ratio, is obtained from these electrodes, particularly using the fingers or hands. The electrodes are standard types and are attached in a conventional manner, e.g. using conducting paste.

Figure 2A:
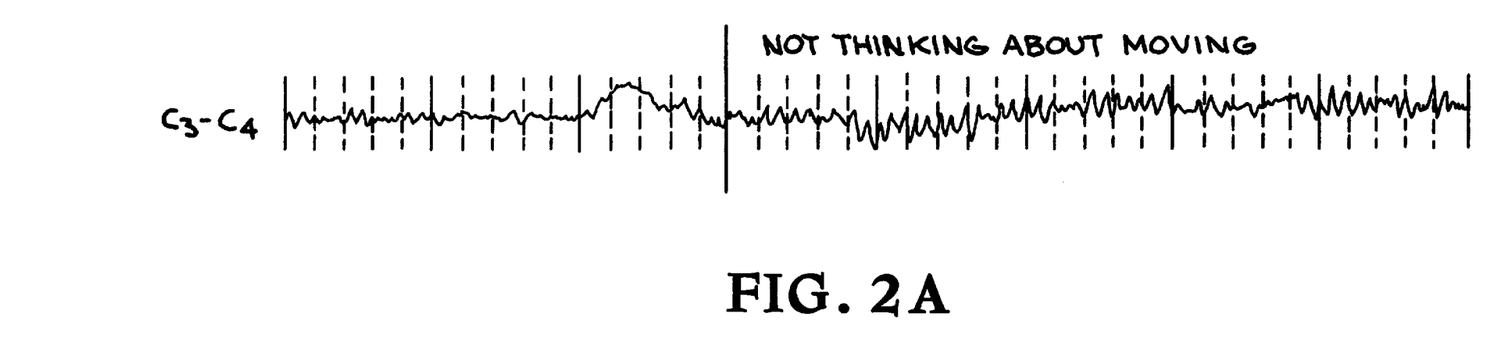
FIGS. 2A and B are graphs of the brain (mu) waves from the motor cortex when not thinking about moving the fingers and when thinking about moving the fingers, respectively.
Figure 2B:
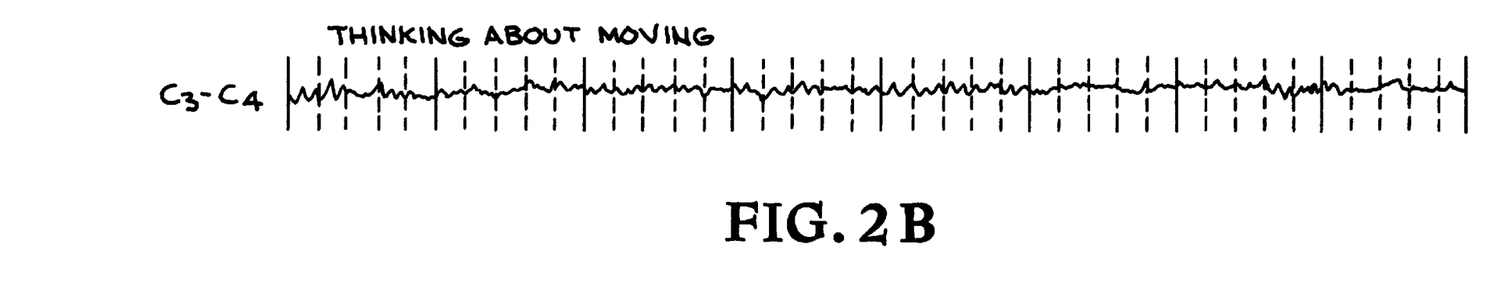

While one is resting (not moving and not thinking about moving), there is a wave in the $C_3$–$C_4$ channel in the 8–13 Hz region known as the mu wave, as shown in FIG. 2A. (While in most persons the mu wave is in the 8–13 Hz range, in a few individuals the range is slightly different, e.g. 8–14 Hz.) The mu wave is severely attenuated, or blocked, by actual movement or the thought of movement (movement rehearsal), as shown in FIG. 2B. To keep the mu wave in the attenuated state the person keeps thinking about moving.

Figure 3A:
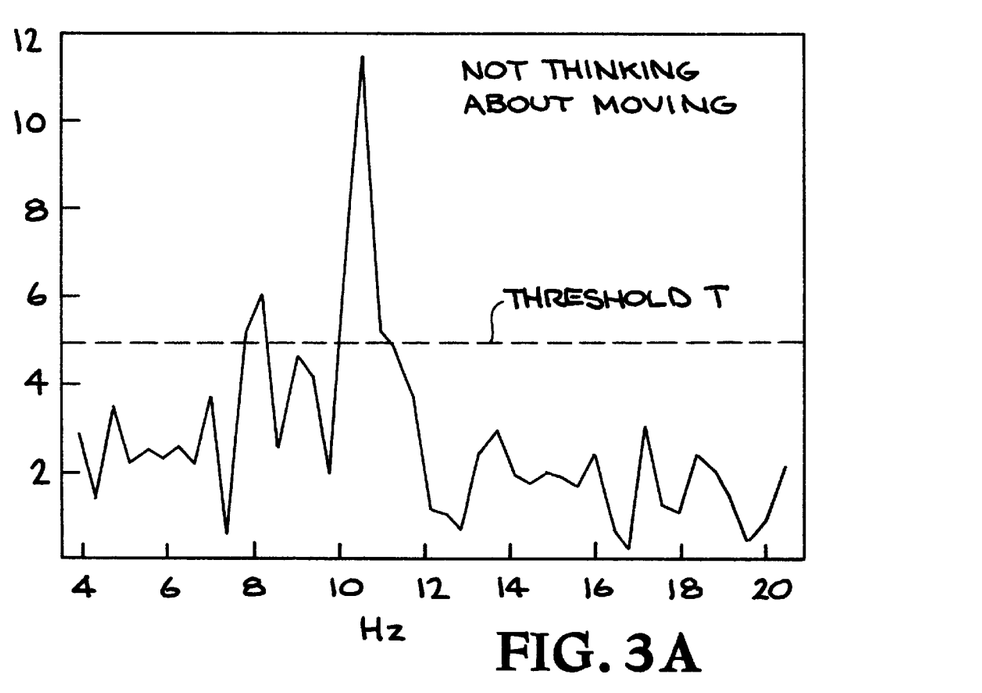
FIGS. 3A and B are the power spectra of the mu waves in FIGS. 2A and B respectively.
Figure 3B:
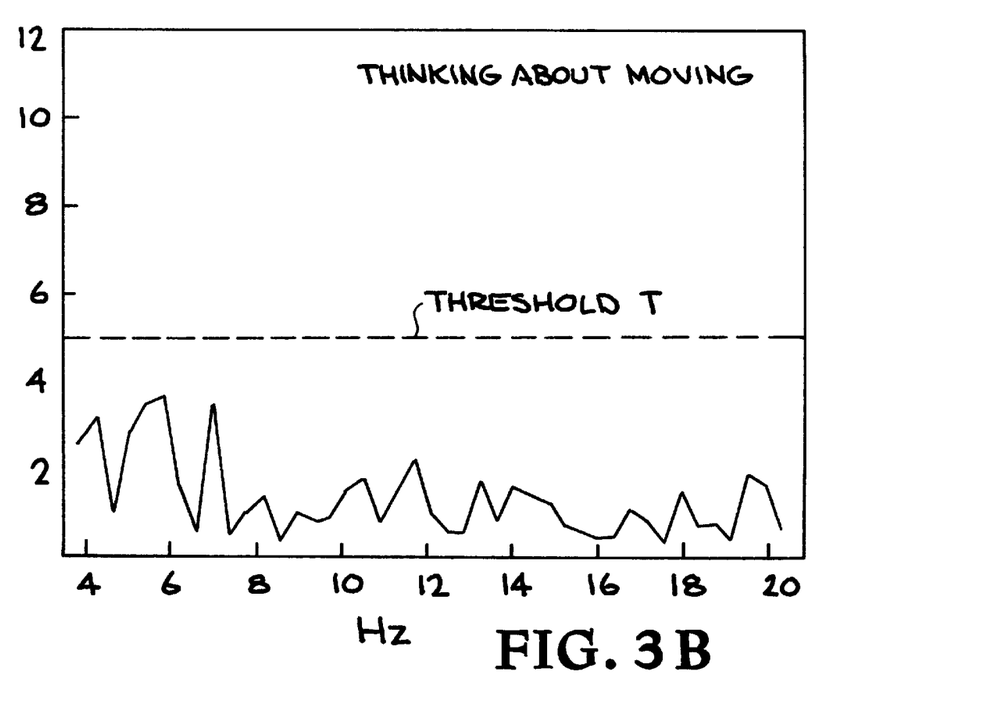

The process of thought detection is automated by using a computer which takes the Fast Fourier Transform (FFT), computes the power spectrum (magnitude squared of the FFT) and finds the peak value in the 8–13 Hz region. The corresponding power spectrum for the EEG (mu) waves in FIGS. 2A and B is shown in FIGS. 3A and B respectively. When a person is moving or thinking about moving, the EEG wave decreases so the peak value of the power spectrum in the 8–13 Hz region is small, as shown in FIG. 3B. When a person is resting, the EEG wave is large, so the peak value of the power spectrum in the 8–13 region is large, as shown in FIG. 3A. Thus the system is a two state system, either above or below a threshold value T between FIGS. 3A and B. Specifically, the peak value of the power spectrum in the 8–13 Hz range for the $C_3$–$C_4$ channel decreases substantially, reliably, and consistently during either movement or movement rehearsal—the thought of movement. Thus, the invention is based on the movement rehearsal paradigm, i.e. the difference in the mu wave between movement or movement rehearsal and rest.

Figure 4A:
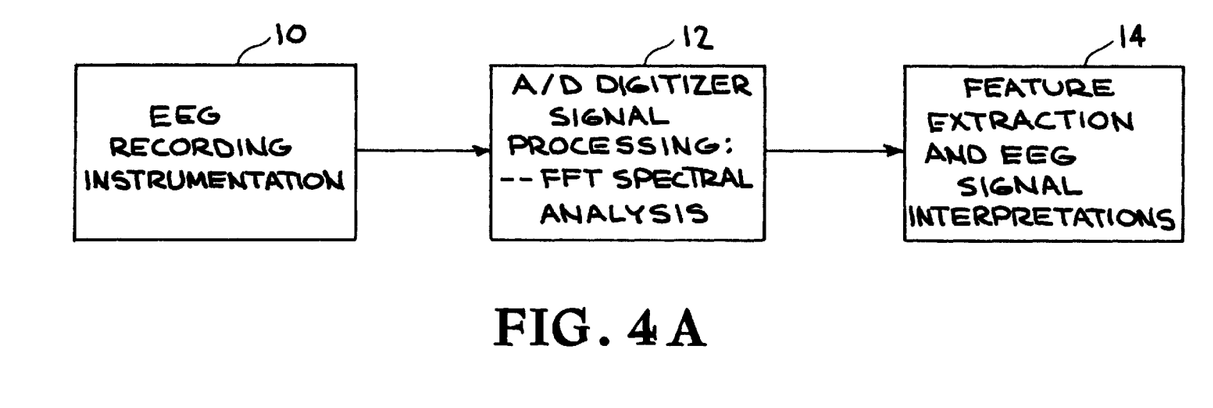
FIGS. 4A and B are block diagrams of the invention, showing the adaptive and operational parts, respectively.
Figure 4B:
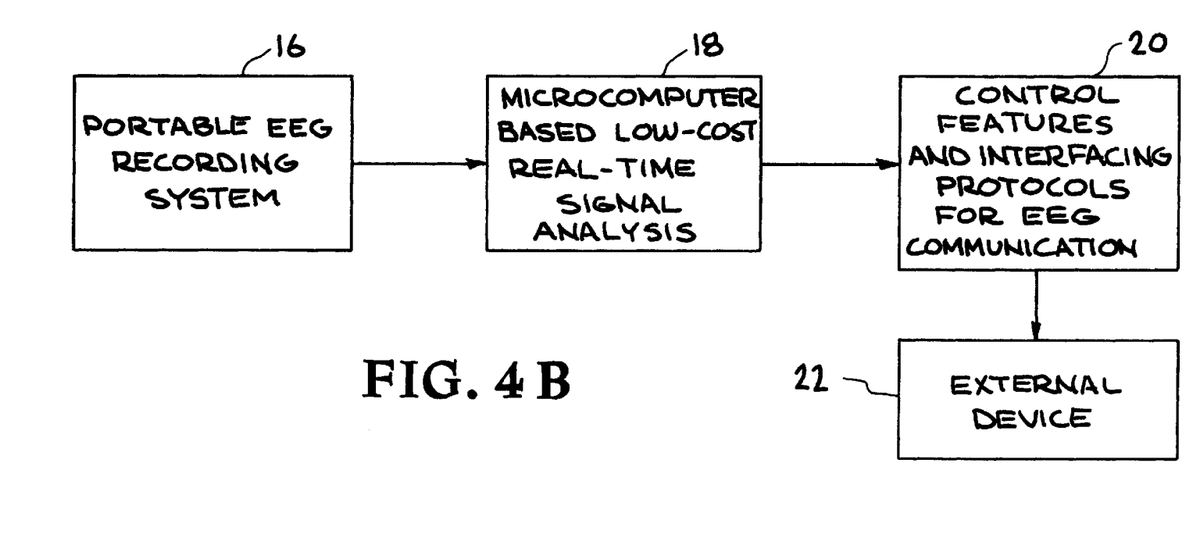

Communication via mu wave blocking associated with finger movement rehearsal is summarized in FIGS. 4A and B. First, baseline data for an individual must be established, using the adaptive part of the system for EEG communication shown in FIG. 4A. The off-line peak value of the power spectrum for a certain time segment, e.g., half a second or a second, in the 8–13 Hz range, is determined while one is resting and while one is thinking about tapping their fingers (or actually tapping their fingers), and a threshold line (as shown in FIG. 3B) is drawn between the high peak power spectrum value during resting, and the lower peak power spectrum value during finger movement rehearsal. As shown in FIG. 4A, mu wave signals from EEG recorder 10 are input into A/D Digitizer/Signal Processor 12 where signal processing, including Fast Fourier Transform (FFT) spectral analysis, is performed. The power spectrum P=|FFT|² for the two cases, movement and rest, is obtained and the threshold T is calculated. The baseline data for interpreting the EEG signals is then extracted from the processed EEG signals in data compilation module 14.

Once the baseline data is obtained, using the adaptive part of the system shown in FIG. 4A, the encephalolexianalyzer can be operated using the operational part of the system shown in FIG. 4B. In the operational mode, EEG recorder 16 is used to detect the mu wave. The EEG signal from recorder 16 is input into microcomputer 18, in which the baseline data obtained from module 14 has been stored. Then in real time the power spectrum of the $C_3$–$C_4$ channel is computed and compared to the stored baseline values, providing an on-off binary signal. The EEG signal can thus be evaluated on a continuous, real-time basis. The resultant signal from computer 18 is input into Controller/Interface 20 which produces a control signal to external device 22.

As described, the system is relatively simple to construct and use, requiring no training and no external operator during the operational phase. Setting the threshold is very easy. The user can operate the system with little effort. The system is assembled from readily available hardware components.

The signal processing to determine high and low peak values of the mu wave power spectrum in response to movement or movement rehearsal includes selecting certain signal time intervals, typically about 1.25 sec, down to about 0.5 sec, to insure system reliability. If the signal is in the high or low state for a sufficient time, then the system will produce a high or low output signal by which the person is able to control a variety of communication and other devices by means of brain waves.

Figure 5A:
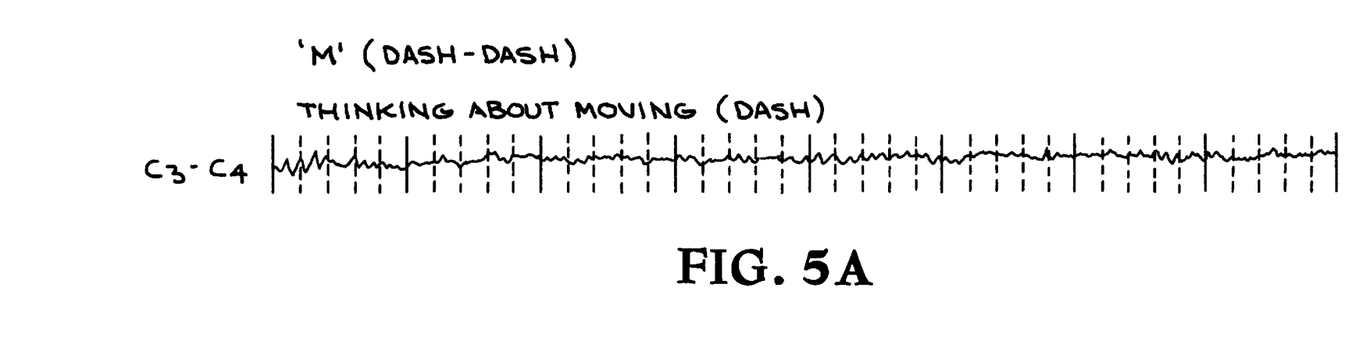
FIGS. 5A, B, C are brain wave recordings showing Morse code communication of the letter M.
Figures 5B, 5C:
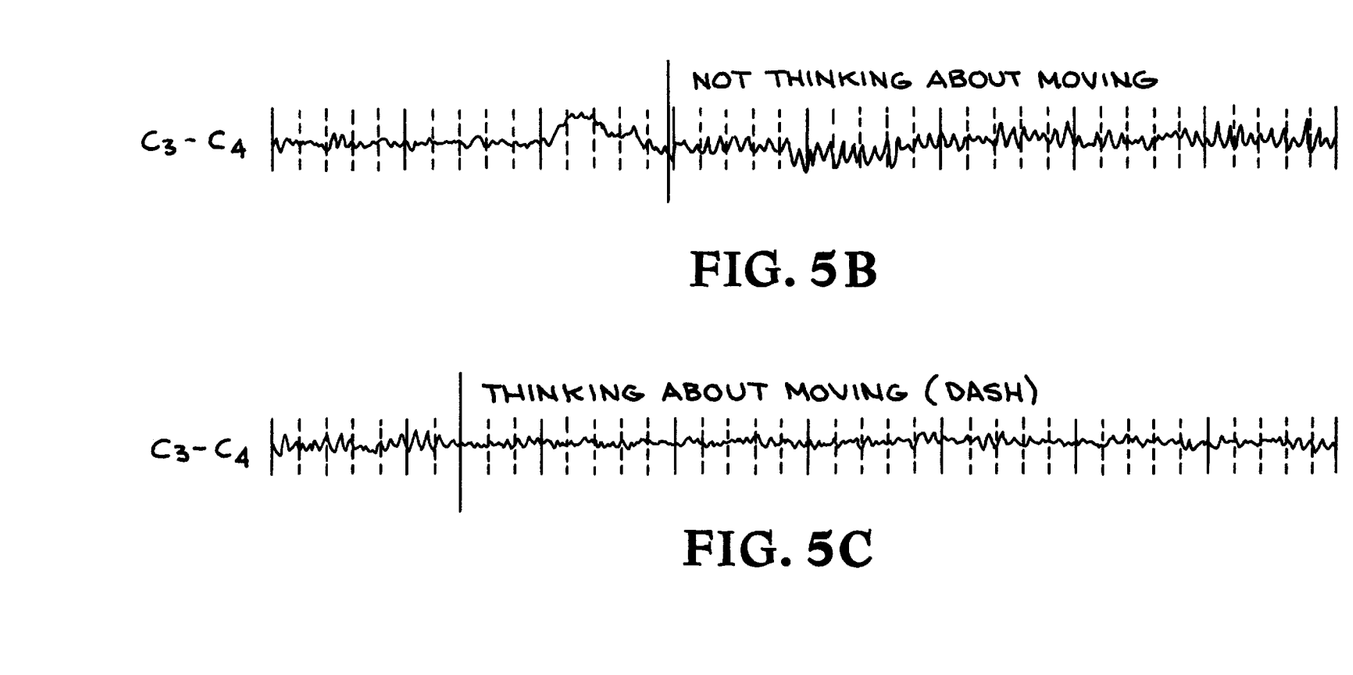

A simple example is a Morse code based communication system. For example, if the peak power spectrum value is below the threshold for a sufficient period of time, a "dot" is typed on a screen, and if the peak power spectrum value is below the threshold for a longer length of time, a "dash" is typed on the screen, thus allowing communication via Morse code. For example, in FIGS. 5A, B, C the subject successfully communicated the letter "M"—dash, dash. FIG. 5A illustrates the first dash, produced by thinking about moving (i.e., low mu wave). This is followed by an interval of high mu wave (not thinking about moving) shown in FIG. 5B. Then a second dash, shown in FIG. 5C, is produced by again thinking of moving. Communication is relatively easy using Morse code or other code where different lengths of the low mu wave state can be used for symbols such as dots and dashes, e.g. a 1 sec dot and a 3 sec dash.

Figure 6A:
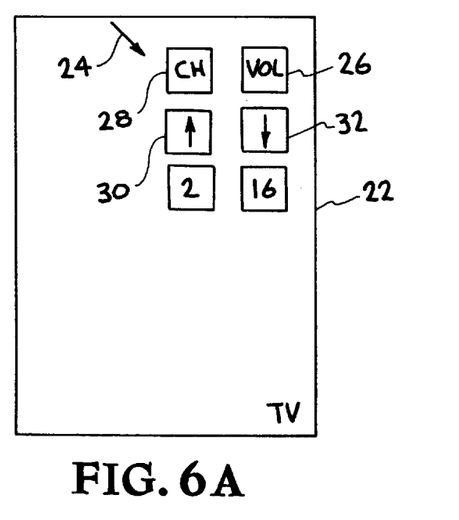
FIGS. 6A and B are schematic views of a TV cursor remotely controlled by brain waves.
Figure 6B:
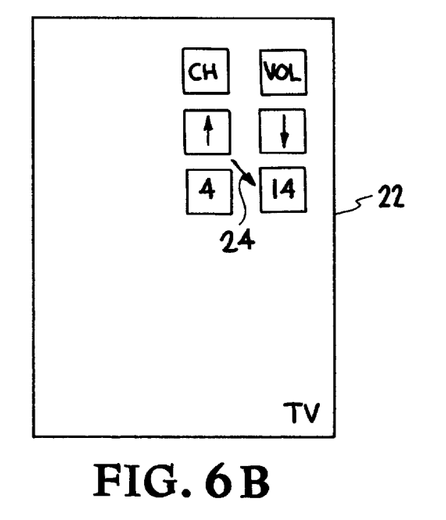

The encephalolexianalyzer can also be used to communicate via cursor controlled remote control. A TV screen with on-screen remote control can be controlled by mu wave blocking associated with finger movement rehearsal, as shown in FIGS. 6A, B. The remote control is first brought on the TV screen 22 by someone thinking about tapping their fingers for a long time. Then a cursor 24 on the screen is controlled by mu wave blocking to adjust the TV.

In the example in FIGS. 6A, B, the remote control can change the channel and/or the volume. When the remote control comes on the screen 22, the cursor 24 is first at the box 26 for volume. If it is desired to change the volume, the person using the system thinks about moving his/her fingers for a short time. If not, the cursor 24 moves to the channel box 28, and if one desires to change the channel, one thinks about moving his/her fingers for a short time and the channel box 28 is selected. Then, the cursor moves to the up box 30; if one desires for the channel to increase, one thinks about moving his/her fingers for a short time and the up box 30 is selected; if not, the cursor 24 moves to the down box 32. Controlling cursor movement via mu wave blocking associated with finger movement rehearsal to choose letters from a grid provides another means of communication using the encephalolexianalyzer.

Another application is thought control of a video game. The mu wave signal is used to control a remote controlled cursor or other mechanism similar to the TV cursor.

The change in power spectrum from movement or movement rehearsal of any body part could be used to actuate the system if a measurable signal change is produced. Finger movement is relatively easy to utilize since finger movement rehearsal provides a large change in the mu wave; fingers on either hand can be used interchangeably. Also another body part such as the foot could be used. The appropriate threshold value can be determined. The $C_3$–$C_4$ electrode pair is particularly suited to control by finger or hand movement or movement rehearsal because they are positioned over the finger/hand region of the motor cortex. The $C_1$–$C_2$ pair, plus the central $C_z$ electrode, are over the toe/foot region so are useful for toe/foot control. However, the foot or toe could be used to produce intermediate mu wave blocking at the $C_3$–$C_4$ pair since the effect is not as great as that from the fingers/hands.

The invention has been described in terms of a simple on-off two state binary system based on mu wave blocking, using only a single channel Ch1 based on the voltage difference $V_{C3}$–$V_{C4}$ measured between electrodes $C_3$ and $C_4$. This electrode pair is used because it provides a better signal to noise ratio than a single electrode.

The signal to noise ratio can be increased by using more than two electrodes. For example, if four electrodes are used—electrodes at $C_3$ and $C_4$, as well as additional electrodes $C_{3'}$ and $C_{4'}$ placed near $C_3$ and $C_4$ respectively as shown in FIG. 1—then the signal to noise ratio can be increased by as much as a factor of the square root of two by considering $(V_{C3}+aV_{C3'})-(V_{C4}+bV_{C4'})$ where a, b are suitably chosen weighing coefficients.

It is possible to detect more than two states, and thus to produce more than a binary control signal. For example, while recording from a pair of electrodes on both sides of the head (one pair on each side) the mu wave can be decreased on one side (contralateral) of the head while not attenuating the mu wave on the other side (ipselateral) of the head, by thinking about moving one hand while thinking about relaxing the other hand. In general, multi-state performance can be achieved by movement or movement rehearsal of one or more body parts while consciously thinking about relaxing one or more other body parts. Also, while recording from the $C_3$–$C_4$ electrodes, or a pair more toward the top of the head such as $C_1$–$C_2$, toe movement rehearsal may be used to cause intermediate mu wave blocking. Movement of the fingers can thus be differentiated from movement of the foot, and even movement of different fingers can be resolved. Multiple thresholds can be established for the power spectra in this case, each one corresponding to a different output control signal. This localization can be used to implement more complex control schemes, e.g. thinking about moving one body part while thinking about not moving other parts.

The difference between right and left signals can be obtained in a two channel system using electrodes $C_3$ and $C_4$ where Ch1=$V_{C3}$–$V_{C3REF}$ and Ch2=$V_{C4}$–$V_{C4REF}$ and each electrode is measured against a reference value. Right and left signals can also be obtained from two pairs of electrodes $C_{3a}$–$C_{3p}$ and $C_{4a}$–$C_{4p}$ placed anteriorly and posteriorly to $C_3$ and $C_4$ as shown in FIG. 1.

Figure 7A:
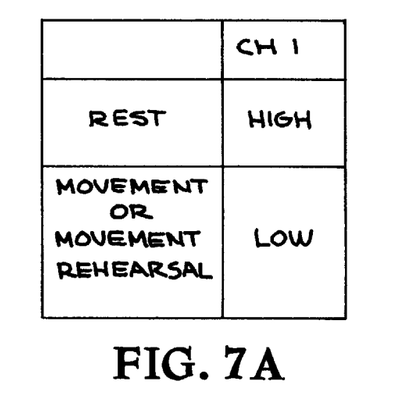
FIGS. 7A and B are state charts of a single channel and a two channel system respectively.
Figure 7B:
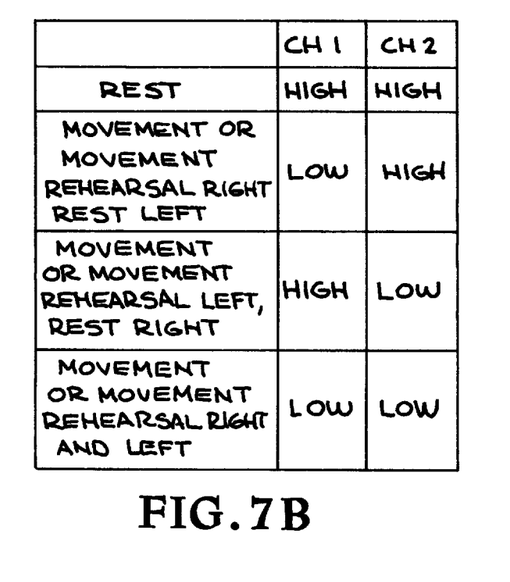

A comparison of the output states between the single and dual channel systems is shown in FIGS. 7A and B. As shown in FIG. 7B, for two body parts, e.g. right and left hand, moving both, resting both or moving one and resting the other, where resting includes thinking about not moving, creates four states. Use of N channels thus provides $2^N$ output states for a more complex control system. N electrodes provides N(N–1)/2 electrode pairs or states. Also extra electrodes can be placed near $C_3$ and $C_4$ to increase signal to noise ratio.

While the invention has been described primarily with respect to pairs of electrodes, a single measurement electrode, e.g. $C_z$, could be used, compared to a reference electrode.

Since the mu wave is substantially attenuated even by slight movements, the encephalolexianalyzer can be used not only for purely thought controlled man-machine communication, but also as a communication channel for people with major motor deficits, but still slightly intact motor abilities.

The encephalolexianalyzer will be of great benefit to people with various handicaps and disabilities, for example, helping people with severe speaking or neurological disorders communicate. The encephalolexianalyzer also has enormous commercial potential, as well as being an invaluable tool for studying the brain. For example, the study of cognitive tasks from the brain is much cheaper, easier and non-invasive than computed tomography (CT), positron emission tomography (PET) or magnetic resonance imaging (MRI).

Changes and modifications in the specifically described embodiments can be carried out without departing from the scope of the invention which is intended to be limited only by the scope of the appended claims.

We claim:

1. Method of producing a communication or control signal using the mu wave from the brain of a person, comprising:

monitoring the mu wave from the brain of the person;

producing changes in the mu wave by performing movement or movement rehearsal by the person of a particular body part or parts of the person to attenuate the mu wave of the person in a selected pattern from the value of the mu wave when the person is neither moving nor thinking of moving;

measuring said mu wave attenuation from the brain of the person caused by movement or movement rehearsal of said body part or parts of the person;

converting said measured mu wave attenuation to a communication or control signal by signal processing the measured mu wave to obtain a power spectrum and comparing the peak power spectrum value to a predetermined threshold value.

2. Method of claim 1 wherein the mu wave is monitored and mu wave attenuation is measured by placing a pair of electrodes on the central region of the scalp, one on each side of the head, in a position to measure the mu wave and measuring a voltage difference between the electrodes.

3. Method of claim 2 wherein the electrodes are placed substantially over the motor cortex.

4. Method of claim 3 wherein the electrodes are placed substantially at the standard EEG $C_3$ and $C_4$ electrode positions.

5. Method of claim 4 wherein a first level of mu wave blocking is measured by movement or movement rehearsal of a finger or hand, and a second level of mu wave blocking is measured by movement or movement rehearsal of another body part.

6. Method of claim 1 wherein the mu wave attenuation is measured in about the 8–13 Hz range.

7. Method of claim 1 wherein the predetermined threshold value is obtained by measuring the mu wave (a) when the person is neither moving nor thinking of moving a body part, and (b) when the person is either moving or thinking of moving a body part; determining the power spectrum of the mu waves from (a) and (b); and selecting a value between the power spectrum from (a) and (b).

8. Method of claim 1 wherein the body part is a finger.

9. Method of claim 1 further comprising selectively attenuating the mu wave for time intervals of varying length by movement or movement rehearsal of said length to produce a control signal having a sequence of time intervals of different lengths.

10. Method of claim 1 wherein mu wave attenuation is measured by placing a pair of electrodes on the central region of the scalp, one on each side of the head and measuring a voltage signal from each electrode, and further comprising differentiating movement or movement rehearsal of a body part from the left and from the right side of the body.

11. Method of claim 1 wherein mu wave attenuation is measured by placing a plurality of electrodes at different positions of the scalp and measuring a voltage signal from each electrode, and further comprising differentiating different parts of the body.

12. Method of claim 11 wherein the plurality of electrodes is more than two and different degrees of mu wave attenuation are measured as a result of movement or movement rehearsal of one body part while consciously thinking about relaxing another body part.

13. Method comprising:

placing a pair of electrodes substantially over the motor cortex of a person's scalp, one on each side of the head;

taking an EEG by measuring a voltage difference signal between the two electrodes;

taking a Fast Fourier Transform (FFT) of the voltage difference signal;

obtaining the power spectrum $P=|FFT|^2$ of the voltage difference signal;

comparing the peak value of the power spectrum of the new wave in the 8–13 Hz range to a baseline value to determine whether the person is either (a) neither moving nor thinking of moving a body part, or (b) either moving or thinking of moving a body part;

producing a binary control signal by changing between (a) and (b).

14. Method of claim 13 wherein the baseline is established by taking an EEG of the person (a) at rest, when the person is neither moving nor thinking of moving a body part, and (b) in movement, when the person is either moving or thinking of moving a body part; taking a Fast Fourier Transform (FFT) of the EEG waves in (a) and (b); obtaining a peak value of the power spectrum of the new wave from the FFT in the 8–13 Hz range; and selecting a threshold value of the peak value of the power spectrum which differentiates (a) from (b).

15. Method of claim 14 wherein the body part is a finger.

16. Method of claim 13 wherein the electrodes are placed substantially at the standard EEG $C_3$ and $C_4$ electrode positions.

17. Method of producing a communication or control signal by an unaided person, comprising:

monitoring the mu wave from the brain of the person;

determining whether the mu wave is above or below a single threshold value, wherein values above the threshold correspond to the person at rest, when the person is neither moving nor thinking of moving a body part of the person, and values below the threshold correspond to movement, when the person is either moving or thinking of moving a body part of the person;

producing changes above and below the single threshold value by alternating between (a) neither moving nor thinking of moving a body part of the person and (b) either moving or thinking of moving a body part of the person, producing a binary communication or control signal from the changes of the mu wave above and below the threshold value.

18. Method of claim 17 wherein the threshold value is determined by measuring (a) a maximum value produced by neither moving nor thinking of moving a body part of the person, and (b) an attenuated value produced by either moving or thinking of moving a body part of the person, and selecting a threshold value between values (a) and (b).

* * * * *